United States Patent
Jequier

(10) Patent No.: US 7,193,082 B2
(45) Date of Patent: Mar. 20, 2007

(54) (6S)-5,6,7,8-TETRAHYDROFOLIC ACID PRODUCTION PROCESS

(75) Inventor: Pascal Jequier, Neuchatel (CH)

(73) Assignee: GMT Fine Chemicals SA (CH)

( * ) Notice: Subject to any disclaimer, the term of this patent is extended or adjusted under 35 U.S.C. 154(b) by 329 days.

(21) Appl. No.: 10/502,615

(22) PCT Filed: Jan. 21, 2003

(86) PCT No.: PCT/EP03/00547

§ 371 (c)(1),
(2), (4) Date: Jul. 23, 2004

(87) PCT Pub. No.: WO03/062239

PCT Pub. Date: Jul. 31, 2003

(65) Prior Publication Data

US 2005/0171348 A1    Aug. 4, 2005

(30) Foreign Application Priority Data

Jan. 25, 2002    (IT) .......................... MI2002A0132

(51) Int. Cl.
*C07D 45/00* (2006.01)
(52) U.S. Cl. ..................................... 544/258
(58) Field of Classification Search ................. 544/258
See application file for complete search history.

(56) References Cited

U.S. PATENT DOCUMENTS 5,234,836 A * 8/1993 Nokihara et al. ........... 544/258
5,489,684 A   2/1996 Jequier et al.
6,596,721 B2 * 7/2003 Muller et al. ............... 514/249

FOREIGN PATENT DOCUMENTS

| EP | 0 348 614 | 4/1991 |
| EP | 0 495 204 | 7/1992 |
| EP | 0 495 204 A1 | 7/1992 |
| EP | 0 537 492 A2 | 4/1994 |
| EP | 0 548 895 | 8/1995 |
| EP | 0 682 026 B1 | 11/1995 |
| EP | 0 600 460 A1 | 2/1996 |
| WO | WO 01/04121 A1 | 1/2001 |

OTHER PUBLICATIONS

Carroll Temple, Jr.; Preparation and Purification of L-()-5,6,7,8-Tetrahydrofolic Acid; American Chemical Society; 1979; pp. 731-734.

* cited by examiner

*Primary Examiner*—Deepak Rao
*Assistant Examiner*—Cecilia Jaisle
(74) *Attorney, Agent, or Firm*—Stetina Brunda Garred & Brucker

(57) ABSTRACT

New process for the production of (6S)-5,6,7,8-tetrahydrofolic acid or derivatives thereof starting from the corresponding (6S, 6R) racemic mixture. The procedure comprises in the steps of adding an organic acid to a non-alkaline suspension of (6S,6R)-5,6,7,8-tetrahydrofolic acid, up to a pH value in the range of 1 to 3; heating the suspension from 30° to 80° C.; cooling the suspension from 20° to 60° C., with selective crystallization of the (6S)-isomer. The procedure gives the (6S)-isomer in high yields and with a high degree of stereoselectivity. It follows that the synthetic access to a large number of pharmacologically active stereoisomers of folic acid is simpler and more-effective.

3 Claims, No Drawings

(6S)-5,6,7,8-TETRAHYDROFOLIC ACID PRODUCTION PROCESS

FIELD OF THE INVENTION

The present invention refers to the synthesis of folic acid derivatives. A new process for the production of (6S)-5,6,7,8-tetrahydrofolic acid is described.

PRIOR ART 5,6,7,8-Tetrahydrofolic acid derivatives have broad therapeutic application, e.g. as antidotes in the cancer therapy with methotrexate or in the antiparasitic therapy or in the treatment of autoimmune diseases, such as rheumatoid arthritis, psoriasis, etc. Out of said derivatives, the best known are 5,6,7,8-tetrahydrofolic acid and 5-formyl-5,6,7,8-tetrahydrofolic acid, also known as leucovorine.

The pharmacological actions of folic derivatives are often influenced by their enantiomeric form. By way of example, the 5,6,7,8-tetrahydrofolic acid contains 2 symmetry centres: one on the glutamic residue (present in L(+) form), the other

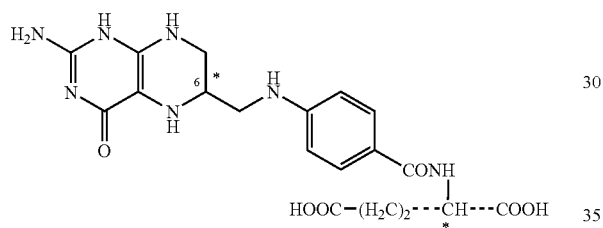

(I)

represented by the carbon in position 6 of the pteridinic ring (see formula (I)).

Therefore, the syntheses of folic derivatives must give the desired isomer selectively and in a high yield. In the case of 5,6,7,8-tetrahydrofolic acid, the desired isomer is generally the isomer with (6S) configuration, which is regarded as being active.

The stereospecific synthesis is carried out using enantioselective reagents and/or including enantiomers resolution procedures, such as the derivatisation and fractional crystallisation. By way of example, European patent application EP-A-495204 discloses a procedure for the separation of the (6S)- and (6R)-isomers of tetrafolic acid, wherein the corresponding racemic acid is converted into an addition salt with sulphonic acids; the sulphonated product is then separated into (6R)- and (6S)-isomers by fractional crystallisation; finally, the sulphonic group is eliminated by treatment with a base. Said procedure includes derivatisation passages to/from sulphonic derivatives, which would entail the use of toxic reagents (e.g. p-toluenesulphonic acid), a process taking a longer time, and the reduction in the final product yields. The production of sulphonic derivatives of tetrahydrofolic acid is also described in patent EP-537492.

Efforts have also been made to obtain the isomers resolution without derivatisation. Patent application EP-A-682026 describes the separation of (6S)- and (6R)-isomers of 5,6,7,8-tetrahydrofolic acid by hydrochloric-acid-induced crystallisation: the process envisages the steps of solubilising the racemic acid with a base up to pH.9, and slowly adding the hydrochloric acid until obtaining a pH value in the range from 3.6 to 6.5, in which range the (6S)-isomer precipitates. At pH values below 3, the product tends to precipitate in the amorphous, non-crystalline, form and the enantiomeric yield of (6S)-isomer decreases drastically. In patent application EP-A-600460, the (6S,6R)-5,6,7,8-tetrahydrofolic acid is treated with hydrochloric acid: at a pH value ranging from 4.8 to 5.3, the (6S)-isomer separation takes place. In this case, the narrow operating range of pH at values just below neutrality, requires a complex pH control. Considering that, as pointed out in the document, at pH values below 4.5 the crystallisation enantioselectivity decreases drastically, the problem of pH control is definitely critical.

Therefore, the need for synthesis procedures of enantiomers of folic acid derivatives involving more easily manageable reaction conditions and giving the desired enantiomers in high yields and with high selectivity is deeply felt.

SUMMARY OF THE INVENTION

A new process for the production of (6S)-5,6,7,8-tetrahydrofolic acid or derivatives thereof starting from the corresponding (6S), (6R) racemic mixture is described. The procedure comprises in the steps of adding an organic acid to a non-alkaline suspension of (6S) (6R)-5,6,7,8-tetrahydrofolic acid, up to a pH value in the range of 1 to 3; heating the suspension from 30° to 80° C.; cooling the suspension from 20° to 60° C. with selective crystallisation of the (6S)-isomer. The procedure gives the (6S)-isomer in high yields and with a high degree of stereoselectivity. It follows that the synthetic access to a large number of pharmacologically active stereoisomers of folic acid is simpler and more effective.

DETAILED DESCRIPTION OF THE INVENTION

It is an object of the present invention to provide a process for isolating the (6S)-5,6,7,8-tetrahydrofolic acid or derivatives thereof from the corresponding racemic mixtures, said process comprises the steps of:

a. adding an organic acid to a non-alkaline suspension of (6S,SR)5,6,7,8-tetrahydrofolic acid or a derivative thereof, until obtaining a pH value in the range from 1 to 3, preferably from 1.4 to 2.0;

b. heating the suspension at a temperature, from 30° to 80° C., preferably from 40° to 60° C.;

c. cooling the suspension at a temperature from 20° to 60° C., preferably from 30° to 40° C.;

and maintaining the pH in steps b. and c. in the range from 1 to 3, preferably from 1.4 to 2.0.

The whole process is preferably carried out in an inert environment, e.g. under nitrogen.

The starting racemic mixture may contain (6S)- and (6R)-isomers in identical or different amounts. The starting racemic 5,6,7,8-tetrahydrofolic acid may be obtained by synthesis procedures already known, e.g. by folic acid reduction (*J. Med. Chem.*, 22, 731, (1979)).

The claimed process does not affect the configuration of the chiral centre on the glutamic residue. It follows that the configuration of said centre in the starting product and in the final product is identical. In a preferred embodiment of the present process, the configuration of the starting racemic mixture and the configuration of the isolated final isomer are L(+): this is the configuration of the glutamic acid found in nature as well as of the therapeutically active folic derivatives.

In the present process, the (6S, 6R)-5,6,7,8-tetrahydrofolic acid or a derivative thereof is suspended in a polar solvent, preferably water. In any case, the pH of the starting racemic suspension must always be lower than or equal to 7, preferably in the range from 3.2 to 5.0. The initial racemic suspension cannot be alkaline or alkalinised with basic substances.

The initial racemic suspension is added with an organic acid, preferably slowly and with stirring, until obtaining a pH value in the range from 1 to 3, preferably of 1.4 to 2.0. The organic acid is generally a weak acid, preferably the citric or tartaric or malic or malonic or succinic acid, the citric and tartaric acids being particularly preferred.

The mixture is heated under stirring at a temperature from 30° to 80° C., preferably from 40° to 60° C.; the heating time (i.e. the time during which the suspension is kept in the aforesaid temperature range) is preferably 15 min at least, and more preferably 30–60 min.

The suspension is then cooled to a temperature preferably ranging from 20° to 60° C., more preferably from 30° to 40° C.; the cooling time, i.e. the time during which the suspension is kept in the aforesaid temperature range, is preferably 10 min at least.

To secure the crystallisation conditions of the (6S) isomer, the pH is appropriately controlled both during the organic acid addition and the successive heating and cooling steps of the suspension. The pH may be controlled by systems already known, e.g. by pHmeters. Too high pH values, if any, may be adjusted by a further addition of organic acid; too low values may be adjusted with NaOH diluted solutions.

The crystallised product is recovered from the solvent by techniques already known, e.g. centrifugation or filtering, followed by washing, etc. Washing is generally performed with aqueous or hydroalcoholic solutions or is performed in different steps with water and an alcoholic solvent.

The claimed process allows the obtainment of the product In high yields (calculated as an enantiomerically enriched product in respect of the initial racemic mixture); the enantiomeric enrichment in the (6S) form is particularly high, as it easily reaches 90% or over. The cyclic repetition of said procedure on the product obtained involves a further enantiomeric enrichment of the product, e.g. up to 98% or over. A further benefit of the invention is that the product is obtained in a stable crystalline form. Furthermore, there is no need to solubilise the initial racemic mixture; consequently, it is also possible to operate with 5,6,7,8-tetrahydrofolic acid amounts exceeding its solubility limit. The present method may be associated with any synthesis of folic derivatives, in particular of 5,6,7,8-tetrahydrofolic acid, requiring the isolation of the (6S)-isomer from the corresponding racemic mixture. Since this step provides high yields, the yields of the processes including it are consequently increased.

The following experimental examples are conveyed by way of indication, not of limitation, of the present invention.

Experimental Part

Racemic 5,6,7,8-tetrahydrofolic acid (THF) was obtained by folic acid reduction as described in literature (*J. Med. Chem.*, 22, 731, (1979)). Racemic THF was isolated by centrifugation under a stream of nitrogen, washed with water, dried under vacuum, kept under nitrogen at −18° C. for less than 48 hrs, and used in the following examples.

EXAMPLE 1

THF (50 g) obtained as described above was suspended in water (150 ml) under nitrogen and the volume was corrected to 300 ml with water, the suspension pH was 3.6. Monohydrated citric acid (92 g) was added portionwise during 15 min under stirring. The mixture was heated to 55° C. under stirring and the pH was adjusted to 1.9 with NaOH 20%. The suspension was diluted to 400 ml with water. The temperature was maintained at 55° C. and the pH value was kept at 1.9 by addition of NaOH 20% during 30 min. The suspension was cooled to 32° C. and stirred for 30 min. The mixture was centrifuged under nitrogen. The cake was washed with 2×15 ml water and 1×30 ml isopropanol, and dried under vacuum. 24.0 g of solid was obtained.

The analysis of the solid gives the following results:

THF content, calculated on anhydrous basis (HPLC): 96%

THF purity higher than 97% of the HPLC area

Water content: 9.9%

Diastereoisomeric ratio: (6S) 87%, (6R) 13%.

EXAMPLE 2

THF (50 g) obtained as described above was suspended in water (150 ml) under nitrogen and the volume was corrected to 300 ml with water; the suspension pH was 3.6. Monohydrated citric acid (92 g) was added portionwise during 15 min under stirring. The mixture was heated to 55° C. under stirring and the pH was adjusted to 1.5 with NaOH 20%. The suspension was diluted to 400 ml with water. The temperature was maintained at 55° C. and the pH value was kept at 1.5 by addition of NaOH 20% during 30 min. The suspension was cooled to 32° C. and stirred for 30 min. The mixture was centrifuged under nitrogen. The cake was washed with 2×15 ml water and 1×30 ml isopropanol, and dried under vacuum. 20.8 g of solid was obtained.

The analysis of the solid gives the following results:

THF content, calculated on anhydrous basis: sample used as standard 100%

THF purity higher than 97% of the HPLC area

Water content 10.4%

Diastereoisomeric ratio: (6S) 89%, (6R) 11%

EXAMPLE 3

THF (50 g) obtained as described above was suspended in water (150 ml) under nitrogen and the volume was corrected to 300 ml with water; the suspension pH was 3.6. Monohydrated citric acid (92 g) was added portionwise during 15 min under stirring. The mixture was heated to 55° C. under stirring and the pH was adjusted to 2.5 with NaOH 20%. The suspension was diluted to 400 ml with water. The temperature was maintained at 55° C. and the pH value was kept at 2.5 by addition of NaOH 20% during 30 min. The suspension was cooled to 32° C. and stirred for 30 min. The mixture was centrifuged under nitrogen. The cake was washed with 2×15 ml water and 1×30 ml isopropanol, and dried under vacuum. 30.7 g of solid was obtained.

The analysis of the solid gives the following results:

THF content, calculated on anhydrous basis (HPLC): 90.6%

THF purity higher than 97% of the HPLC area

Water content: 9.5%

Diastereoisomeric ratio: (6S) 77%, (6R) 23%

EXAMPLE 4

THF (50 g) obtained as described above was suspended in water (150 ml) under nitrogen and the volume was corrected to 300 ml with water; the suspension pH was 3.6. Monohydrated citric acid (46 g) was added portionwise during 15 min under stirring. The mixture was heated to 55° C. under stirring and the pH was adjusted to 1.9 with NaOH 20%. The suspension was diluted to 400 ml with water. The temperature was maintained at 55° C. and the pH value was kept at 1.9 by addition of NaOH 20% during 30 min. The suspension was cooled to 32° C. and stirred for 30 min. The mixture was centrifuged under nitrogen. The cake was washed with 2×15 ml water and 1×30 ml isopropanol, and dried under vacuum. 24.2 g of solid was obtained.

The analysis of the solid gives the following results:
THF content, calculated on anhydrous basis (HPLC): 89.2%
THF purity higher than 97% of the HPLC area
Water content: 9.8%
Diastereoisomeric ratio: (6S) 85%, (6R) 15%

EXAMPLE 5

THF (50 g) obtained as described above was suspended in water (150 ml) under nitrogen and the volume was corrected to 300 ml with water; the suspension pH was 3.6. L(+) tartaric acid (90 g) was added portionwise during 15 min under stirring. The mixture was heated to 55° C. under stirring and the pH was adjusted to 1.7 with NaOH 20%. The suspension was diluted to 400 ml with water. The temperature was maintained at 55° C. and the pH value was kept at 1.7 by addition of NaOH 20% during 30 min. The suspension was cooled to 32° C. and stirred for 30 min. The mixture was centrifuged under nitrogen. The cake was washed with 2×15 ml water and 1×30 ml isopropanol, and dried under vacuum. 19.3 g of solid was obtained.

The analysis of the solid gave the following results:
THF content, calculated on anhydrous basis (HPLC): 98.9%
THF purity higher than 97% of the HPLC area
Water content: 9.5%
Diastereoisomeric ratio: (6S) 91%, (6R) 9%

EXAMPLE 6

THF (300 g) obtained as described above was suspended in water (1000 ml) under nitrogen and the volume was corrected to 1800 ml with water, the suspension pH was 3.6. Monohydrated citric acid (550 g) was added portionwise during 15 min under stirring. The mixture was heated to 55° C. under stirring and the pH was adjusted to 1.9 with NaOH 20%. The suspension was diluted to 2400 ml with water. The temperature was maintained at 55° C. and the pH value was kept at 1.9 by addition of NaOH 20% during 30 min. The suspension was cooled to 40° C. and stirred for 30 min. The mixture was centrifuged under nitrogen. The cake was washed with 2×30 ml water and 1×40 ml isopropanol, and dried under vacuum. 138 g of solid was obtained.

The analysis of the solid gives the following results:
THF content, calculated on anhydrous basis (HPLC): 98%
THF purity higher than 97% of the HPLC area
Water content: 9.5%
Diastereoisomeric ratio: (6S) 91%, (6R) 9%

The invention claimed is:
1. Process for selectively crystallizing the (6S)-5,6,7,8-tetrahydrofolic acid from the corresponding racemic mixtures, comprising the steps of:
   a. adding a weak organic acid, selected from citric, tartaric, malic, malonic and succinic acids, to a non-alkaline suspension of (6S,6R)-5,6,7,8-tetrahydrofolic acid, until obtaining a pH value in the range from 1 to 3;
   b. heating the suspension from step a. at a temperature from 40° to 60° C.;
   c. cooling the suspension from step b. at a temperature from 30° to 40° C.; and maintaining the pH in steps b. and c. ion the range from 1 to 3.

2. The process according to claim 1, wherein the pH in steps a., b., c. is comprised in the range from 1.4 to 2.0.

3. The process according to claim 1, wherein said organic acid is citric acid or tartaric acid.

* * * * *